United States Patent [19]

Winter

[11] 4,331,145
[45] May 25, 1982

[54] MULTIPLE SCLEROSIS TREATMENT

[76] Inventor: Arthur Winter, 44 Holly Dr., Short Hills, N.J. 07078

[21] Appl. No.: 229,045

[22] Filed: Jan. 28, 1981

[51] Int. Cl.$^3$ ............................................. A61B 17/36
[52] U.S. Cl. ............................... 128/207.21; 128/1 R; 424/177
[58] Field of Search .................. 424/177; 128/207.21, 128/1 R

[56] References Cited

U.S. PATENT DOCUMENTS

| | | | |
|---|---|---|---|
| 3,864,481 | 2/1975 | Hashim | 424/177 |
| 4,113,858 | 9/1978 | Hashim | 424/177 |
| 4,230,696 | 10/1980 | Hashim | 424/177 |

OTHER PUBLICATIONS

Lahdesmaki & Vahvelainen, "Aromatic Amino Acid Supply and Brain Protein Synthesis", 1974, Assoc. Scientific Publishers, N.Y., pp. 283-284.
Winter, Use of TNS in Treatment of MS, 1976, J. Am. Ass.of Neuroserg Nurses, Dec. vol. 8, No. 2, pp. 125-131.
Thompson, Fatty Acid Metabolism in MS, Bioch. Soc. Symp. vol. 35, pp. 103-111, 1973.
Solar, Transcut, Electroanalgesia & Naloxone, Neurologia, 1978, vol. 24, 415-417.
Komi et al. Skeletal Musc. Fib. and Musc. Enzy Act in Monozygous and Digzgous Twins of Both Sexes, Acta Physiol. Scand., 1977, 100, 385-392.
Winter, Pain Relief—Transcutaneous Nerve Stim., J. of Med. Soc. of N.J., May 1971, vol. 71, No. 5, pp. 365-367.

*Primary Examiner*—Robert W. Michell
*Assistant Examiner*—Nancy A. B. Swisher
*Attorney, Agent, or Firm*—Wolder, Gross & Yavner

[57] ABSTRACT

A treatment regime is described for multiple sclerosis comprising transcutaneous neuro-stimulation (TNS) and oral administration of d-phenylalanine. The d-phenylalanine prolongs the improvement from the TNS.

5 Claims, No Drawings

MULTIPLE SCLEROSIS TREATMENT

FIELD OF INVENTION

This invention relates to a treatment regime for multiple sclerosis and more particularly to a regime that involves the combined application of transcutaneous electrical nerve-stimulation (TNS) and the internal administration of dosage units of d-phenylalanine or its precursors.

BACKGROUND OF THE INVENTION

The exact causes of multiple sclerosis are unknown. However, there is no doubt that there exists some conductive malfunction of the nerves, particularly the central nervous system. Neuropathologically, multiple lesions of the central nervous system (never the peripheral nervous system), are seen.

The general course of the disease among patients is characterized by exacerbation and remission of symptons. Such variations are almost indicative of the disease.

The disease is world-wide, but is most prevalent in temperate and cold climates. There appears to be no racial factor in the disease, but it is noted as more prevalent in females. Overt symptomology appears usually between the ages of 20 and 40 years. The disease affects an estimated half million Americans.

Etiological hypotheses for the disease, based on epidemiology, range from slow viruses, and immune system anomolies to heavy metal and esoteric metal poisonings. Some basis for each of these hypotheses have been found, but no incontrovertable proof has been forthcoming for any specific one or group.

Gross microscopic appearance of the brain and chord is often normal, but plaques of irregular grayish matter and grey areas may be seen in the white matter of the brain, brain stem and the ventricles, particularly the lateral and third ventricles. The size of these lesions from section to section of the spinal chord has been found in some cases to invade the entire cross-section of the chord. Also, it has been noted that there is a similarity between the demyelination of multiple sclerosis and the demyelination in pernicious anemia.

Microscopic examination of the lesions indicate demyelinazation of the nerve fibers. There is localized destruction of the myelin sheath, some damage to axis cylinders, proliferation of the glial cells and blood vessel changes. However, the ground structure appears preserved despite the fact that the microglial cells proliferate and phagocytize the debris, producing both fibrils and gross sclerotic changes.

The onset of symptoms may be acute with spasm paresthesias (prickling sensation), diplopia (double vision), amblyopia (dimmed vision), vertigo (dizziness) and hemiplegia (paralysis of one side of the body). Initially, the symptoms characteristically vary from day to day and shift from one extremity to another. The spinal form is often a spastic paraplagia, but frequently with intact cutaneous sensation. About 40% of the pateients have bladder dysfunction with urgency and incontinence.

Mental disturbances, primary or secondary, are found in about 95% of the cases—usually depression, but occasionally compensating euphoria and/or emotional liability.

During the choronic phase, Charcots' triad of scanning speech, intention tremor and nystagmus is often exhibited. Vertigo, ataxia and visual loss may precede the other symptoms much before a definitive diagnosis is possible.

Epidemiologically, it has been noted that about 40% of patients with retrobulbar neuritis (inflammation of the optic nerve at its junction with the eyeball) at ages 20 to 45 years will develop multiple sclerosis in 10 to 15 years. This is presently being intensively studied.

Two useful procedures are available diagnostically. The hot-bath test and individual eye examinations with Ishihara or pseudoisochromatic AO plates to detect alteration in color vision.

Alterations in color vision may occur even in patients who have never had a decrease or loss in visual acuity. The finding of such abnormalities points to an initial subclinical optic neuropathy caused by a lesion of the optic nerve. Such a finding supports the criterion of multiplicity of lesions for multiple sclerosis.

The hot-bath test is performed by immersing the patient in a hot bath (40° C.). This test may cause the appearance of latent new symptoms and recurrence of previously experienced but undocumented transient symptoms and signs. Because of the intensity of the exacerbated symptoms, the patient must be under constant supervision during this test. Diplopia, loss or diminution of visual acuity, nystagmus, paresthesiae, changes in relfexes and Babinski signs may be demonstrated at this time. All these signs and symptoms regress once the patient has cooled so that the hot bath test may be considered as harmless.

These two tests are useful in that the single most important criterion in the diagnosis of multiple sclerosis is the demonstrated presence of *more than one* lesion of the central nervous system. The hot bath is useful in evoking the multiple latent effects of such lesions.

After such physical tests, chemical tests, for additional confirmation, are directed to such phenomena as the presence of oligoclonal bands in the gamma-globulin region upon electrophoresis of cerebrospinal fluid. This test is positive and identifying in 90% of patients with multiple sclerosis.

Recently greater insight has been afforded into the physiology of pain, its nature, its perception and its function under normal and diseased conditions by the discovery and study of endorphins and enkaphalins. The reactions of these compounds with, and at various sites along the nerves, the brain stem and the brain; have provided perspective as to nerve impulse conduction under normal and diseased conditions. Pain perception, pseudo-perception, exogenous and endogenous stimulation and their chemical effects, pinpoint the effects of demyelinization of the nerve fibers in the clinical course of the multiple sclerosis syndrome.

From these studies, it is now apparent that whether it is an electrolyte imbalance; demyelinization; anti-body reaction; alteration of receptor members, sites or nature; the impairment of nerve transmission to specific sites and muscles results in the muscular dysfunction seen in multiple sclerosis. To use an electrical analogy, the faulty switching, misdirection and imbalance of circuits causes the characteristic inability to use the proper and intended muscles due to spasm, pain or lack of properly directed stimulation as compared to normal nerve transmission.

In multiple sclerosis there is an obvious decrease in ascending and descending electrical transmission along nerves that are pathologically changed by demyelinization. It has been shown that demyelinized fibers do not transmit well so that nerve signals are delayed, misdirected or completely interrupted.

The electrical deficit thus noted has been the subject of my recent studies. I have previously found that degrees of relief of symptomatic pain are afforded by biphasic square wave nerve stimulation (Jr Med. Soc. N.J. Vol. 71 #5 pg. 365-367 May 74). Recently, it has been shown that such stimulation is related to the pain-perception mediation involving endorphins. The relationship of endorphin release in pain mediation by acupuncture, electro-acupuncture and transcutaneous nerve-stimulation (TNS) has recently been explored and confirmed by naloxone blocking and endorphin assay (B. Sjolund; L. Terenius; M. Eriksson; Acta physiol Scand 1977 #100 pp 382-384).

Recently, I have found that the electrical nerve conduction anomalies, painful as well as functional, as found in multiple sclerosis, can to some extent be reconstituted or mitigated by a course of TNS. In multiple sclerosis patients normal or near normal short term transmission and control is made possible by TNS treatment despite impairment due to demyelinization. Polarization and depolarization take place along the affected fibers. There appears to be a potentiation of the fibers despite the demyelinization areas of the nerve and spinal chord. This provides some short-term improvement in overt multiple sclerosis symptoms following the cessation of supply of electrical stimulation.

However, the remissions of specific symptoms, while immediate, are usually transient. In certain instances, the symptoms have returned within 24-48 hours, more extended relief is usually noted and in some cases the TNS treatment appears to have stimulated other remission mechanisms resulting in extended periods of relief.

THE INVENTION AND ITS OBJECTS

It has been an object throughout my research in the lab, in the clinic and in surgery, to provide relief for as long as possible to sufferers from multiple sclerosis.

It is another object to further extend the improvements and remissions normally obtained by TNS treatment.

The objectives are achieved by administering unit dosages of d-phenylalanine concomitantly and subsequently to courses of transcutaneous neuro-stimulation (TNS).

TNS is a pulsed current generated by a device originally devised by Shealy for control of benign pain by dorsal column stimulation. Shealy found that wave forms, square wave and spike wave were equally effective. The battery operated transcutaneous neuro-stimulator had been used as a screening test to determine the suitability of patients for surgical implant or placement of dorsal column stimulators.

On the basis of a serendipitous screening test on a carcinoma patient with concomitant multiple sclerosis; movement in a plegic extremity with reduction of spasticity as well as pain was noted. On the basis of this finding, TNS treatment courses were applied to a series of 135 patients. All showed subjective and objective improvement to varying degrees on a 0 to +4 scale. While only two cases showed +4 (100% improvement), the majority of patients had varying degrees of improvement, mainly clustered from +1 (25%) to +2 (50%). There were no controlled studies because the first cases showed immediate reduction in pain and spasticity. It was felt to be inhumane to withhold this therapeutic means merely in the interest of scientific "purity".

As pointed out above with TNS, the excellent results of mitigation and/or remission were primarily of a temporary nature requiring repeated TNS courses to maintain improvement. On the average, the improvement lasted for about one to two weeks. Repeating the treatment at required intervals has maintained the improved states in the group for observed periods in excess of three years.

The TNS generator device (TNS—Neuromod Mfg. by Medtronics Inc. Minneapolis, Minn.) is a pulsed current source which is adjustable from 0 to 76 ±15% milliamps measured into a 500 ohm load. The voltage is limited to 100 volts and the pulse rate is variable up to 200 cps. Usually the TNS was applied for about 2-30 minutes at 6-15 milliamps pulsed at 8 cps.

The TNS was administered via electrodes placed between the chord and the source of the pathology. If there is paraplagia or paraparesis, then two electrodes are placed over the paravertebral area in the sacrum. If the dysfunction is in the upper extremities, the electrodes are positioned over the posterior aspect of the ipsilateral trapezium and deltoid muscles.

In order to extend the effectiveness of each course of TNS, various approaches were taken. Review of the effects of prostaglandin inhibitors such as aspirin and indomethacin showed no advantage in combined therapy. Classically, the analgesic narcotics have little place in multiple sclerosis therapy due to resulting reduced motor function as well as the need for avoidance of habituating drugs in long term debilitating diseases.

Recently, Ephrenpreis et al (Proc.2nd Int. Congress on Pain; Montreal, Canada, August 1978) have reported on d-phenylalanine and hydrocinnamic acid (d,l-phynylalanine) and d-leucine which are endorphin related mild analgesics. The relationship in action to the endorphins is deduced from their analgesic potency reversal by naloxone. The mechanism of action is postulated on the inhibition of carboxypeptidase, the body enzyme which normally shortens and controls the activity of the endorphins. On the basis of this noted activity, it was decided to try oral administration of the non-toxic vital aminoacid, d-phenylalanine in conjunction with TNS.

Two double blind series of tests were run. The first consisted of six patients, the seconds series included 10 patients. All the patients received 15 to 30 minutes TNS at 8 pulses/sec. and 6 milliamps. The electrodes were appropriately positioned to the patients symptomology. The same day that the TNS was administered, the oral administration of matched capsules of d-phenylalanine or placebo was started and maintained for seven days. The patients were re-examined at the end of the oral therapy, (one week after the TNS) and then one week later. The examinations included subjective interviews and objective evaluation by the physician. Improvement over TNS was found in 66% of medicated patients in the first series and 100% in the second series. A 33 and 10% mild placebo effect improvement was noted in the placebo-medicated TNS-treated patients.

As agreed at the onset with the participating patients, the placebo-treated controls were then retreated with TNS and received the d-phenylalanine. These patients all exhibited positive response to the medication by both subjective and objective evaluation.

In addition, comprehensive clinical trials of the combined therapy of the invention was initiated. The initial trial series included 54 multiple sclerosis patients. All had confirmed diagnosis and the course of the disease ranged from spastic paraparesis of varying degrees, plegia, and cerebellar ataxia. The duration of the condition was from 3 to 37 years. Of the 54 patients included, 46 showed improvement. Included in this group were the cross-overs of the unmedicated patients in the double-blind study. An important improvement, both subjectively reported and objectively noted, was bladder control. This is an important social and patient care factor and accounted for vastly improved patient morale. Some patients noted improved muscle tone, as in the hand grip. This was confirmed on the dynamometer. Other patients noted improved locomotion including distances able to be traversed on crutches.

Over all, the treated patients had less depression, greater mobility and improved bladder control, all these improvements were of longer duration than improvements obtained with TNS alone.

Another effect noted by a number of patients is an increased resistance to viral infections, such as colds and influenza. Also, those who caught infections noted they were less severe in intensity and shorter in duration.

In light of the noted similarity of demyelination in both multiple sclerosis and pernicious anemia, as previously noted, and due to the similarity in both conditions of postulated remyelination upon remission as well as other similarities in symptomology, I have also, in a selected group, added Vitamin $B_{12}$, 1000 micrograms, daily to the therapy. The basis of this further combination in therapy is that there may be a malabsorption of the amino-acid d-phenylalanine in multiple sclerosis as noted by Thompson, R. H. S.: "Fatty Acid Metabolism in Multiple Sclerosis" Biochemical Society Symposium, 1973 pp. 103–111. The combination of cynacobalamin ($B_{12}$) may enhance the absorption of the amino acid by the intestinal wall and thus may make both essential compounds available for remyelination. Initial clinical improvements have been noted, but specific proofs of the postulated mechanisms are not yet available. Specific protocols for unambiguous proof have not yet been developed.

In one patient to whom naloxone was administered after repeated combined therapy according to this invention, no reduction in clinical improvement was noted. This indicated that the treatment of this invention, while related to endorphin, as regards pain, probably achieves its effects via different mechanisms in improving the nerve conduction anomalies of multiple sclerosis. A possible mechanism may be the inhibition of the immune response after administration of phenylalanine; reported by Byan, W. (JAMA Vol. 191 #4 pg. 119, 120, July 25, 65) also (cf. Salsr, G.: Modification De L'Action Antalgique de L'electrotherapic transcutanee apres Traitement avec Naloxone, Neurochirurgic 1978, 24 pp. 415–417).

A possible explanation of this anomaly—the improvement despite administration of the endorphin-blocking nalaxone—may lie in the combined effects of TNS and d-phenylalanine on spasms induced by brain damage. I have recently noted a marked improvement in an accident victim suffering from brain-damage induced spasms. These subsided and substantially disappeared for extended periods following a course of TNS and d-phenylalanine as set forth above. Apparently, the treatment of this invention while having some effect on the conduction of sensory impulses (ascending signals), has a more significant effect on the motor pulses (descending signals). The TNS-induced potential or polarization at the injured portions of the nerve improves spasm control. This physical or chemical condition either mobilizes or utilizes the d-phenylalanine to maintain proper conduction; or conversely, d-phenylalanine is an amino-acid involved in the neuromechanisms of spasm and TNS provides sites for its normal function (which may be interfered by demyelinazation).

No matter which theory is correct, either those discussed above or yet to be derived from the observed facts, a marked improvement is obtained in multiple sclerosis patients with the treatment of my invention. I do not feel bound to any specific explanation, but merely wish to provide a safe and effective treatment for the relief of patients suffering from multiple sclerosis. My treatment is, of course, capable of combination with other presently accepted modes of therapy for this disease and generally is not contra-indicated by any of the usual treatments and adjunct therapies.

I have not seen any side-effects of either multiple sclerosis or my invention which have required discontinuance of my therapy in a wide spectrum of multiple sclerosis patients.

The combined TNS/d-phenylalanine treatment may also be useful generally in spasm caused by CNS dysfunction or by brain damage, but at present insufficient clinical data is at hand.

What is claimed is:

1. A method of treating patients exhibiting symptoms of multiple sclerosis to reduce spasm and permit more normal functioning which comprises the steps of administering a course of treatment which includes transcutaneous neurostimulation and concomitant and subsequent administration of oral doses of d-phenylalanine for at least a period of time sufficient to extend the therapeutic effects of the transcutaneous neurostimulation.

2. The method according to claim 1 wherein the d-phenylalanine doses for an adult are 250 mgm. administered three times daily for at least one week.

3. The method according to claim 1 wherein the transcutaneous neurostimulation consists of substantially square wave pulses, at up to 100 cps, administered at the rate of from five to ten pulses per second, at five to fifteen milliamps, for from five to thirty minutes, via skin electrodes positioned between the spinal chord and the source of the pathology.

4. The method according to claim 1 wherein additionally, a daily dosage of cyanocobalamin is administered.

5. The method according to claim 4 wherein the adult dosage of the cynacobalamin is 1,000 micrograms daily by subcutaneous route.

* * * * *